United States Patent
Lesser et al.

(10) Patent No.: US 6,248,126 B1
(45) Date of Patent: Jun. 19, 2001

(54) TECHNIQUE FOR USING HEAT FLOW MANAGEMENT TO TREAT BRAIN DISORDERS

(75) Inventors: Ronald P. Lesser, Towson; W. Robert S. Webber, Ellicott City, both of MD (US)

(73) Assignee: The Johns Hopkins University, Baltimore, MD (US)

( * ) Notice: Subject to any disclaimer, the term of this patent is extended or adjusted under 35 U.S.C. 154(b) by 32 days.

(21) Appl. No.: 09/228,414

(22) Filed: Jan. 12, 1999

Related U.S. Application Data

(60) Provisional application No. 60/071,312, filed on Jan. 12, 1998.

(51) Int. Cl.[7] ............................... A61F 7/12; A61F 7/00; A61B 18/18
(52) U.S. Cl. ............................... 607/113; 607/96; 607/99; 606/20; 606/21; 606/27
(58) Field of Search ............................... 607/113, 98, 99, 607/96; 606/21, 20, 27

(56) References Cited

U.S. PATENT DOCUMENTS

| | | | |
|---|---|---|---|
| 3,170,465 | * | 2/1965 | Henney et al. ............ 128/401 |
| 4,719,919 | * | 1/1988 | Marchosky et al. ............ 128/401 |
| 4,989,601 | | 2/1991 | Marchosky . |
| 5,540,737 | | 7/1996 | Fenn . |
| 5,611,767 | | 3/1997 | Williams . |
| 5,916,242 | * | 6/1999 | Schwartz ............ 607/113 |

OTHER PUBLICATIONS

Callaghan, et al., "Cerebral Effects of Experimental Hypothermia", A.M.A. Archives of Surgery, 1954, 68, pp. 208–215.

Wass, et al., "Hypothermia–associated Protection from Ischemic Brain Injury: Implications for Patient Management", pp. 95–111.

Frizzell, et al., "Effects of Etomidate and Hypothermia on Cerebral Metabolism and Blood Flow in a Canine Model of Hypoperfusion", Journal of Neurosurgical Anesthesiology, vol. 5, No. 2, pp. 104–110.

(List continued on next page.)

*Primary Examiner*—Linda C. M. Dvorak
*Assistant Examiner*—Jocelyn Debra Ram
(74) *Attorney, Agent, or Firm*—Pillsbury Winthrop LLP

(57) ABSTRACT

A method of treating a brain disorder by heat transfer from brain tissue comprising the steps of surgically cutting a heat transfer aperture into a patient's skull, thereby exposing a predetermined portion of patient's brain; surgically implanting into said heat transfer aperture a heat pump having one or more electrical sensor elements and one or more temperature sensor elements; surgically implanting a heat transfer management unit in a body cavity of said patient such that a micro controller of the heat transfer management unit is connected to one or more activity sensor elements and one or more temperature sensor elements contacting brain tissue and connecting the heat transfer management unit to said heat pump via a lead bundle. Optionally, the heat transfer unit may be located external to the patient's body. Responsive to signals from one or more activity or temperature sensor elements, mathematical algorithms of the heat transfer management unit determine abnormal brain activity, causing the heat pump to remove heat from the brain tissue into a heat sink, thereby cooling the predetermined portion of the patient's brain. This technique utilizes acute hypothermia by means of a Peltier cooler or similar device to cool the brain temperature to reduce or prevent seizure initiation and/or propagation. The method may be used in association with brain stimulation and/or drug application to acutely avoid the occurrence of a seizure episode.

21 Claims, 3 Drawing Sheets

OTHER PUBLICATIONS

Koizumi, et al., "Effect of Hypothermia on Excitability of Spinal Neurons", Neurophysiol, vol. 23, 1960, pp. 421–431.

Tasaki, et al., "Action Currents of Single Nerve Fibers as Modified by Temperature Changes", Neurophysiol, vol. 11, 1948, pp. 311–315.

Fay, "Early Experiences with Local and Generalized Refrigeration of the Human Brain", Neurosurg, vol. 16, 1959, pp. 239–260.

Kawakami, et al., "The Influence of Temperature on the Balance Between the Excitatory and Inhibitory Cerebral Systems. A Contribution to the Caudate–Hypothalamic Antagonism", Electroenceph. Clin. Neurophysiol., 1963, 15: pp 230–237.

Chatfield, et al., "The Effects of Temperature on the Spontaneous and Induced Electrical Activity in the Cerebral Cortex of the Golden Hamster", EEG Clin. Neurophysiol., 1951, 3: pp225–230.

Bindman, et al., "Comparison of the Effects on Electrocortical Activity of General Body Cooling and Local Cooling of the Surface of the Brain", Electroenceph. Clin. Neurophysiol. 1963, 15: pp. 238–245.

de Jong, et al., "Nerve Conduction Velocity During Hypothermia in Man", Anesthesiology, vol. 27, No. 6, Nov.–Dec. 1966, pp. 805–810.

Ferrari, et al., "Convulsive Electrocortical Discharges in Hypothermic Dog", p. 441.

Scott, et al., "The Effect of Lowered Body Temperature on the EEG", EEGJ, vol. 5, 1953, p. 465.

Jia, et al., "Cold Injury to Nerves is not Due to Ischaemia Alone", Brain (1998), 121, pp. 989–1001.

Michenfelder, "Barbiturates for Brain Resuscitation: Yes and No", Anesthesiology, vol. 57, No. 2, Aug. 1982, pp. 74–75.

Marion, et al., "The Use of Moderate Therapeutic Hypothermia for Patients with Severe Head Injuries: a Preliminary Report", J. Neurosurg 79: 1993, pp. 354–362.

Weinstein, et al., "Hypothermia and Electrical Activity of Cerebral Cortex", Archives of Neurology, vol. 4, Apr. 1961, pp. 441–448.

Hagerdal, et al., "Protective Effect of Combinations of Hypothermia and Barbiturates in Cerebral Hypoxia in the Rat", Anthesthesiology, vol. 49, No. 3, Sep. 1978, pp. 165–169.

Noell, et al., "Effects of Cold Exposure on Brain Activity", Federation Proceedings, vol. 11, p. 114.

Dietrich, et al., "Post–Traumatic Brain Hypothermia Reduces Histopathological Damage Following Concussive Brain Injury in the Rat", Acta Neuropathol (1994) 87: pp. 250–258.

Rosomoff, "Hypothermia and Cerebral Vascular Lesions", A.M.A. Archives of Neurology and Psychiatry, vol. 78, Nov. 1957, pp. 454–464.

Michenfelder, et al., "The Effects of Anesthesia and Hypothermia on Canine Cerebral ATP and Lactate during Anoxia Produced by Decapitation", Anesthesiology, Oct. 1970, vol. 33, No. 4, pp. 430–439.

Milde, et al., "Cerebral Functional, Metabolic, and Hemodynamic Effects of Etomidate in Dogs", Anesthesiology, vol. 63, No. 4, Oct. 1985, pp. 371–377.

Suda, et al., "Analysis of Effects of Hydrothermia on Central Nervous System Responses", pp. 373–380.

Gaenshirt, et al., "The Electrocorticogram of the Cat's Brain at Temperatures Between 40° C. and 20° C.", EEG Clin. Neurophysiol., 1954, 6: pp. 409–413.

Ommaya, et al., "Extravascular Local Cooling of the Brain in Man", J. Neurosurgery, vol. 20, 1963, pp. 8–20.

Berntman, et al., "Cerebral Protective Effect of Low–Grade Hypothermia", Anesthesiology, 55:, 1981, pp. 495–498.

Clifton, et al., "Marked Protection by Moderate Hypothermia After Experimental Traumatic Brain Injury", Journal of Cerebral Blood Flow and Metabolism, 11:, 1991, pp. 114–121.

Minamisawa, et al., "The Effect of Mild Hyperthermia and Hypothermia on Brain Damage Following 5, 10, and 15 Minutes of Forebrain Ischemia", Annals of Neurology, vol. 28, No. 1, Jul. 1990, pp. 26–33.

Marion, et al., "Treatment of Traumatic Brain Injury with Moderate Hypothermia", The New England Journal of Medicine, vol. 336, No. 8, Feb. 20, 1997, pp. 540–546.

Gunn, et al., "Selective Head Cooling in Newborn Infants After Perinatal Asphyxia: A Safety Study", Pediatrics, vol. 102, No. 4, Oct. 1998, pp. 885–892.

Gunn, et al. "Neuroprotection With Prolonged Head Cooling Started Before Postischemic Seizures in Fetal Sheep", Medical Economics, Jun. 15, 1998:36, pp. 1098–1106.

Busto, et al., "Effect of Mild Hypothermia on Ischemia–Induced Released of Neurotransmitters and Free Fatty Acids in Rat Brain", Stroke, vol. 20, No. 7, Jul. 1989, pp. 904–910.

Todd, "The Neurologic Effects of Thiopental Therapy Following Experimental Cardiac Arrest in Cats", Anesthesiology, 57:, Aug. 1982, pp. 76–86.

Clifton, et al., "A Phase II Study of Moderate Hypothermia in Severe Brain Injury", Journal of Neurotrauma, vol. 10, No. 3, 1993, pp. 263–271.

Kopf, et al., "Central Nervous System Tolerance to Cardiac Arrest during Profound Hypothermia", Journal of Surgical Research, vol. 18, No. 1, Jan. 1975, pp. 29–34.

Kramer, et al., "The Effect of Profound Hypothermia on Preservation of Cerebral ATP Content During Circulatory Arrest", Journal of Thoracic and Cardiovascular Surgery, vol. 56, No. 5, Nov. 1968, pp. 699–709.

Pomeranz, et al., "The Effect of Resuscitative Moderate Hypothermia Following Epidural Brain Compression on Cerebral Damage in a Canine Outcome Model", J. Neurosurg. vol. 79, Aug. 1993, pp. 241–251.

Clasen, et al., "Hypothermia and Hypotension in Experimental Cerebral Edema", Arch Neurol., vol. 19, Nov. 1968, pp. 472–486.

Owens, "Effect of Hypothermia on Seizures Induced by Physical and Chemical Means", pp. 560–562.

Marion, et al., "Treatment of Experimental Brain Injury with Moderate Hypothermia and 21–Aminosteroids", Journal of Neurotrauma, vol. 13, No. 3, 1996, pp. 139–147.

Busto, et al., "Small Differences in Intraischemic Brain Temperature Critically Determine the Extent of Ischemic Neuronal Injury", Journal of Cerebral Blood Flow and Metabolism, vol. 7, No. 6, 1987, pp. 729–738.

Denys, "AAEM Minimonograph #14: The Influence of Temperature in Clinical Neurophysiology", American Association of Electrodiagnostic Medicine, Sep. 1991, pp. 1–23.

Stevenson, et al., "Effects of Induced Hypothermia on Subcortical Evoked Potentials in the Cat", pp. 423–426.

Scott, "The EEG during Hypothermia", EEG Journal, vol. 7, 1955, p. 466.

Ferrari, et al., "Convulsive Electrocortical Discharges in Hypothermic Dog", EEG Journal, vol. 7, 1955, p 441.

Marshall, et al., "Temporary Circulatory Occlusion to the Brain of the Hypothermic Dog", A.M.A. Archives of Surgery 72:, 1956, pp. 98–106.

Sedzimir, "Therapeutic Hypothermia in Cases of Head Injury", Journal of Neurosurg. vol. 16, 1959, pp. 407–414.

Frondel, "Reports", Science, vol. 124, Nov. 9, 1956, pp. 931–932.

Lee, et al., "Intraoperative Hippocampal Cooling and Wada Memory Testing in the Evaluation of Amnesia Risk Following Anterior Temporal Lobectomy" Arch Neurol, vol. 52, Sep. 1995, pp. 857–861.

Essman, et al., "Audiogenic Seizure in Genetically Susceptible Mice: Relation of Hypothermia to Onset and Susceptibility", Experimental Neurology, vol. 9, 1964, pp. 228–235.

Battista, "Effect of Cold on Cortical Potentials in the Cat", Experimental Neurology, vol. 19, 1967, pp. 140–155.

Vastola, et al., "Inhibition of Focal Seizures by Moderate Hypothermia", Arch Neurol., vol. 20, Apr. 1969, pp. 430–439.

Lafferty, et al., "Cerebral Hypometabolism Obtained with Deep Pentobarbital Anesthesia and Hypothermia (30C)", Anesthesiology, vol. 49, No. 3, Sep. 1978, pp. 159–164.

Massopust, et al., "Cortical and Subcortical Responses to Hypothermia", Experimental Neurology, vol. 9, 1964, pp. 249–261.

Lipp, "Effect to Deep Hypothermia on the Electrical Activity of the Brain", Electroenceph. Clin. Neurophysiol., vol. 17, 1964, pp. 46–51.

Swinyard, et al., "Effects of Alterations in Body Temperature on Properties of Convulsive Seizures in Rats", Amer. J Physiol., vol. 154, Aug. 1948, pp. 207–210.

Koella, et al., "The Influence of Temperature Changes on the Electrocortical Responses to Acoustic and Nociceptive Stimuli in the Cat", EEG Journal, vol. 6, 1954, pp. 629–634.

Gaenshirt, et al., "Suppression of the Cat's Brain at Temperatures Between 40°C. and 20°C.", EEG Journal, vol. 6, 1954, pp. 409–413.

Nemoto, et al., "Suppression of Celebral Metabolic rate for Oxygen ($CMRO_2$) by Mild Hypothermia Compared with Thiopental", Journal of Neurosurgical Anesthesiology, vol. 8, No. 1, 1966, pp. 52–59.

Botterell, et al., "Hypothermia in Neurosurgery", Part IV, pp. 363–368.

Meyer, et al., "Effects of Hypothermia on Local Blood Flow and Metabolism During Cerebral Ischemia and Hypoxia", J. Neurosurg., vol. 14, 1957, pp. 210–227.

Vacanti, et al., "Mild Hypothermia and Mg++ Protect Against Irreversible Damage During CNS Ischemia", Stroke, vol. 15, No. 4, 1984, pp. 695–698.

Smith, et al., "Mild Pre– and Posttraumatic Hypothermia Attenuates Blood–Brain Barrier Damage Following Controlled Cortical Impact Injury in the Rat", Journal of Neurotrauma, vol. 13, No. 1, 1996, pp. 1–9.

Young, et al., "The Effect of Graded Hypothermia on Hypoxic–Ischemic Brain Damage: A Neuropathologic Study in the Neonatal Rat", Stroke, vol. 14, No. 6, 1983, 929–934.

Buchan, et al., "Hypothermia But Not the N–Methyl–D–Aspartate Antagonist, MK–801, Attenuates Neuronal Damage in Gerbils Subjected to Transient Global Ischemia", The Journal of Neuroscience, 10(1), Jan. 1990, pp. 311–316.

Woodhall, et al., "The Physiologic and Pathologic Effects of Localized Cerebral Hypothermia", Annals of Surgery, vol. 147, No. 5, May 1958, pp. 673–683.

* cited by examiner

TECHNIQUE FOR USING HEAT FLOW MANAGEMENT TO TREAT BRAIN DISORDERS

This application claims the benefit of U.S. Provisional Application No. 60/071,312, filed Jan. 12,1998.

BACKGROUND OF THE INVENTION

1. Field of the invention

The invention pertains to acute methods of treating a brain disorder using heat transfer to improve brain function. Heat transfer may be combined with electrical stimulation of the brain or direct infusion of therapeutic agents into the brain to reduce or prevent the occurrence of, for example, an epileptic seizure. The method may also be used for brain disorders other than epilepsy, for spinal disorders, and for disorders of other body organs and tissues.

2. Description of Related Art

Epilepsy is a significant medical problem, as nearly 1% of the United States population is affected by this disease at any given time, constituting about 2.6 million people. The incidence of epilepsy is higher in children and in the elderly, such that approximately 3.5% of the population will have epilepsy at some point in life[1, 3, 20, 21]. Seizures are controllable in 70% of patients, but about 30% of patients have seizures refractory to treatment. Estimates indicate that the total lifetime costs in 1990 dollars for all of those with epilepsy newly diagnosed just in 1990 will be 3 billion dollars with slightly over 1 billion of this direct costs and the rest indirect costs. For those having controllable seizures, the cost per patient will be slightly over $4000. The figure rises to about $138,000 for patients with persistent, intractable, lifelong epilepsy. In 1991 dollars, the direct costs for the treatment of epilepsy in the United States were 1.8 billion dollars and the indirect costs amounted to 8.5 billion dollars[1, 3]. Thus, the disorder is a significant health problem and a need exists for improved treatments to control the disease and alleviate its burden on society as a whole.

Epileptic seizures occur because of an abnormal intensity and synchronized firing of brain cells. Generalized seizures can begin over essentially the entire brain at one time, while others, known as focal or partial seizures, begin in a localized area of the brain and then spread. Thus, both widespread and localized mechanisms appear to be involved in the occurrence of seizures. As an example, seizures manifest themselves as seizure discharges affecting the cerebral cortex, the outer most layer of the brain, though paradoxically, stimulation of the thalamus and other subcortical regions, located deeper within the brain, have been shown to not only initiate but also control or even prevent seizures. Evidence suggests that the thalamus and the substantial nigra are involved in the development of certain kinds of seizures[15, 9, 41, 39, 13]. Even more widespread mechanisms might be involved, as evidenced by the successful use of vagal nerve stimulation for treatment of some seizures. The vagus nerve is located in the neck and extends to the brain stem from which it has widespread connections within the brain, including branches to the thalamus[32, 22]. Studies have shown that chronic vagal nerve stimulation can reduce seizures by 50% or more in a third of treated patients[14, 4]. A vagal nerve simulator has recently been released as a commercial product. Information thus far indicates that it is moderately effective, but only rarely controls seizures completely.

In some patients, seizures are sufficiently localized such that removal of a particular area of the brain may result in complete seizure control[11]. Electrical stimulation provides a non-surgical means for impairing generation of localized seizures[38, 32, 34, 27]. In experimental animal models, drug application to a seizure focus can suppress or eliminate seizure activity[10, 28, 16, 24, 33].

Hypothermia is known to have a protective effect on the brain both in experimental animal preparations and in humans[5, 31, 8, 29, 18, 19]. This protective effect on the brain is one of the reasons for employing hypothermia in medical procedures, such as cardiac surgery[6]. Hypothermia alters the electrical activity of the cortex in models of brain ischemia, and decreases the production of the excitatory neurotransmitters glutamate and dopamine[7]. Hypothermia also appears to reduce the occurrence, frequency, and amplitude of cortical potentials and suppresses seizure activity[35, 12, 2, 40]. Cooling is thought to prevent or abort seizures by reducing cortical excitability. Cooling brain tissue can be safely accomplished when properly undertaken. For example, irrigation of the temporal horn of the lateral ventricle with ice-cold liquid to cool the hippocampus has been successful in acutely altering memory functions in humans with no apparent adverse effects[25].

Prevention of seizures using any of these methods implies that one knows when a seizure is occurring. Numerous of approaches toward detection of seizures have been explored[36, 37, 17, 26, 30, 38, 23, 42, 43]. One potential method utilizes neural networks as a means of detecting seizures. The advantage of this approach is that the computer detection may be modified to suit the individual patient. Implanted electrodes may use an algorithm based on neural networks to detect seizure activity. Alternatively, several rule based or template matching methods for seizure detection may be employed, as well as methods modeling seizures as chaotic attractors.

U.S. Pat. No. 5,713,923 to Ward et al. (Ward '923) discloses techniques for treating epilepsy using a combination of electrical stimulation of the brain and drug infusion to neural tissue. Stimulation may be directed to increase the output of inhibitory structures, such as the cerebellum, thalamus, or brain stem, or may inactivate epileptogenic areas. These methods tend to be based on chronic stimulation of brain inhibitory systems, with the goal of decreasing the background propensity to epileptogenesis. Historically, stimulation of inhibitory structures alone has not been particularly successful in seizure management. Ward '923 uses an implantable electrode to sense seizure onset, which permits regulatable stimulation of the brain during initial seizure activity. The combination of drug infusion with brain stimulation as disclosed in Ward '923, however, would fail to be effective in many types of seizures. Many drugs are not particularly stable at body temperature, rendering them unsuitable for long term storage in an implanted infusion device. Certain risks exist for patients receiving the combined therapy of Ward '923, including an increased risk for seizure propagation due brain stimulation as well as drug related side effects. Thus, while suitable for controlling some seizures, a substantial population of patients have seizures which cannot be treated using the methodology of Ward '923.

Therefore, a need exists to improve the therapeutic options available to persons with brain disorders, such as epilepsy.

SUMMARY OF THE INVENTION

An object of the present invention relates to the use of hypothermia for the treatment of brain disorders, comprising a method of treating a brain disorder by heat transfer from brain tissue comprising the steps of:

surgically cutting a heat transfer aperture into a patient's skull, thereby exposing a predetermined portion of patient's brain;

surgically implanting into said heat transfer aperture a heat pump having one or more activity sensor elements and one or more temperature sensor elements;

surgically implanting a heat transfer management unit in a body cavity of said patient such that a micro controller of the heat transfer management unit is connected to one or more activity sensor elements and one or more temperature sensor elements contacting brain tissue; and connecting the heat transfer management unit to said heat pump via a lead bundle;

whereby responsive to signals from said one or more activity or temperature sensor elements, mathematical algorithms of the heat transfer management unit determine abnormal brain activity, causing the heat pump to remove heat from the brain tissue into a heat sink, thereby cooling the predetermined portion of the patient's brain.

In a preferred embodiment, the invention relates to a method of reducing or preventing the occurrence of a seizure comprising cooling brain tissue at or near a seizure focus or a brain structure that modulates seizures.

In another preferred embodiment, the invention relates to a method of reducing or preventing the occurrence of a seizure comprising cooling brain tissue and electrically stimulating the brain at or near a seizure focus or a brain structure that modulates seizures.

In yet another preferred embodiment, the invention relates a method of reducing or preventing the occurrence of a seizure comprising cooling brain tissue and infusing a therapeutic agent into the brain at or near a seizure focus or a brain structure that modulates seizures.

In still another preferred embodiment, the invention relates a method of reducing or preventing the occurrence of a seizure comprising cooling brain tissue and electrically stimulating the brain tissue and infusing a therapeutic agent into the brain at or near a seizurefocus or a brain structure that modulates seizures.

The invention provides for placing electrodes in or on the brain area(s) of seizure foci and using mathematical algorithms to detect seizure onset. Once seizure onset is detected, cooling of the brain tissue is initiated to reduce abnormal brain cell firing. The electrodes detecting seizure occurrence could be situated on the cortical surface, deeply within cortex inaccessible to a surface electrode, or in deeper, subcortical areas of the brain such as the thalamus. Similarly, cooling and other treatments could occur at the cortex, could occur in subcortical regions, or both. The invention provides for multiple techniques that could be applied singly or in combination depending upon the situation of the specific seizure. Control of an individual event may require only one of these methods, or may require a combination of two or more procedures involving, for example, hypothermia and drug infusion together with electrical brain stimulation. Because single or combination techniques are provided, the likelihood of seizure control is improved, as therapy may be tailored to individual patient needs. The overall amount of treatment would be decreased to the minimum necessary, as the method would only treat patients when a seizure is imminent or occurring.

Yet another preferred embodiment provides for the control of brain disorders such as intractable pain, psychiatric disorders and movement disorders. Examples of such ailments include dystonia or tremor, manic-depressive illness, panic attacks, and psychosis which may manifest themselves by acute changes in behavior.

Yet another preferred embodiment provides for control of central nervous system swelling and inflammation. For example, swelling of brain or spinal tissue due to trauma, hemorrhage, encephalitis or localized myelitis, mass lesions, such as tumors, cysts, and abscesses, and intractable migraine headaches may be controlled by cooling according to the invention.

Still another preferred embodiment of the invention provides for control of swelling, inflammation or localized pain in non-central nervous system organs.

These and other features and advantages of the invention will become apparent from the detailed description below and from the accompanying drawings.

DESCRIPTION OF PREFERRED EMBODIMENTS

Figure 1:
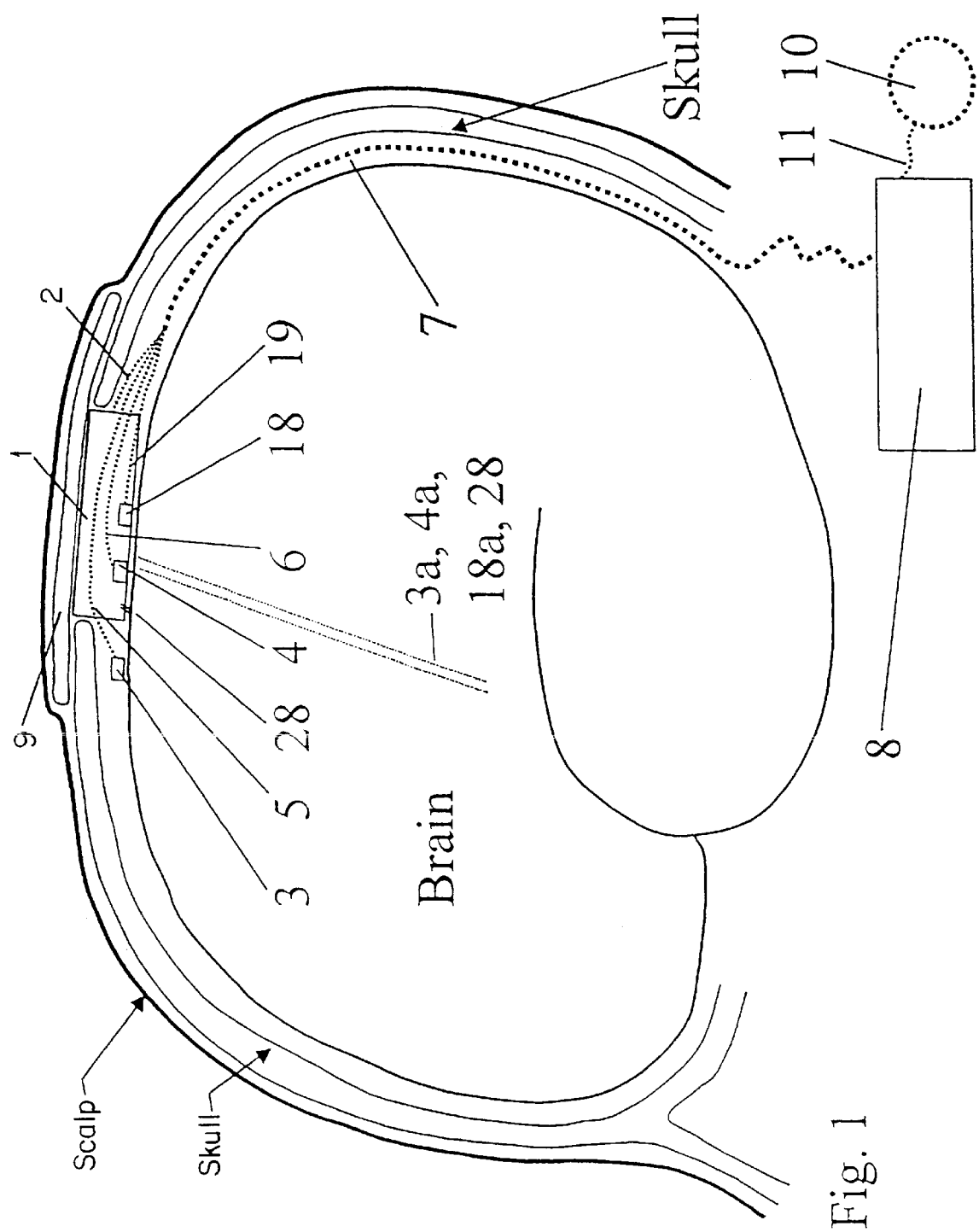
FIG. 1 shows the main components of the invention. A heat transfer aperture (HTA) is surgically cut into the patient's skull. Thereafter, a heat pump is placed in this aperture. The device is located on the brain surface to treat superficial foci, such that the HTA rests on the surface of the section of brain to be treated. Treatment of a portion of the brain below the surface is achieved by placement of the HTA at a convenient location on the brain surface, with tubing leading to the deeper brain area to be treated. The relationship of the heat pump to the brain, skull and scalp is shown for the preferred embodiment of the invention. A lead bundle connects the heat pump to the heat transfer management unit (HTMU) located in a suitable body cavity.

An embodiment of the invention relates to hypothermia in combination with brain stimulation as a treatment of brain disorders, such as epilepsy. This may be accomplished by stimulating a brain structure which modulates seizures. Modulation is defined herein as increasing or decreasing neuronal excitability of a brain region responsible for producing seizures. Brain structures targeted for stimulation may be inhibitory or excitatory in nature. For example, the output of inhibitory structures, such as the cerebellum, thalamus, or brain stem, may be increased via brain stimulation to inhibit the firing of cells in a seizure focus located elsewhere.

Another aspect of the invention is to target regions in which a treatment could directly block epileptogenic activity. Such targets include the hippocampus, the neocortex, and subcortical and brain stem regions. Different targets are expected to be important in different types of brain disorders. For example, patients having unilateral hippocampal onset epilepsy may consider hippocampal removal, but the surgery exposes some of these patients to potential memory impairment. Such patients may benefit from the lower risk hypothermia and electrical brain stimulation procedure of the invention. In other patients suffering from bilateral hippocampal disease, hypothermia and electrical stimulation might be an effective treatment, as unilateral hippocampal removal would not be useful and bilateral removal is not an option due to memory concerns.

The hypothermia and brain stimulation treatment of the invention may be achieved by stimulating brain areas constantly, or at fixed intervals. Feedback driven stimulation from brain monitoring of seizure patterns or pre-seizure patterns is also suitable according to the invention, such that treatment to prevent perpetuation or spread of seizure patterns may be administered upon detection of seizure activity. For example, altered neural discharges in the hippocampus, amygdala, neocortex or elsewhere may be present at the onset of a seizure. Such patterns often occur locally, but may spread before a seizure clinically manifests. These alterations could be detected and mitigated or eliminated with stimulation in combination with hypothermia. Patients often experience auras as perceived warnings of impending seizures. In fact, auras are very small seizures that do not progress to alter consciousness. Hypothermia and stimulation may block the spread of such auras. Consequently, a patient would be able to drive and engage in other normal daily activities. Stimulation may also interfere with synchronization of ictal firing. Synchronization or recruitment of multiple brain areas into a seizure pattern is very much related to the spread of seizure activity in the brain. Thus, either chronic stimulation or feedback-based episodic stimulation could impair synchronization and thus prevent seizure development.

An aspect of the invention entails systematically evaluating neocortical ictal firing patterns and determining methods of interfering with these patterns. These patterns and activities have been extensively monitored through clinical epilepsy monitoring centers. Firing patterns differ among patients such that no one pattern can be expected to occur in all patients with epilepsy. Systematic evaluation of the firing pattern will allow optimization of treatment for each patient. Brain cell activity may be monitored by electrical or chemical sensing elements (activity sensing elements) contacting brain structures to detect abnormal neuronal firing patterns.

Placement of the electrodes to target seizure foci similarly may be patient specific, according to the invention. EEG recordings indicate that some seizures begin at the cortical surface, while others originate deep within internal brain structures, such as the hippocampus, amygdala, and thalamus. Although seizures may occur as a purely subcortical phenomenon, most epileptologists believe seizures involve the cortex, but may be triggered by or may secondarily involve thalamo-cortical circuits. Thus, both cortical and subcortical stimulation could abort, or control, seizures, but different sites would have to be stimulated in different patients to be effective. In addition to the above-mentioned brain structures, other subcortical regions, such as the area tempesta and the caudate nucleus, have been found to be important areas for seizure initiation or propagation in some situations, and thus may be target areas for therapeutic intervention.

The invention also provides for placement of a catheter or similar tubing into the brain or direct delivery of drugs to a seizure focus or a brain structure which modulates seizure activity. When combined with controlled hypothermia, the direct infusion of drugs into the brain may reduce or prevent the occurrence of seizures. Examples of medication useful in the invention include such therapeutic agents as hydantoins, deoxybarbiturates, benzodiazepines, glutamate receptor agonists, glutamate receptor antagonists, γ-aminobutyric acid receptor agonists, γ-aminobutyric acid receptor antagonists, dopamine receptor agonists, dopamine receptor antagonists and anesthetics.

Acute and chronic animal models of epilepsy, such as kindling and cobalt/estrogen/penicillin models, suggest that hypothermia combined with brain stimulation and/or direct neural drug infusion will successfully control brain disorders in humans.

The invention provides for the control of brain disorders such as intractable pain, psychiatric disorders and movement disorders. Ailments including dystonia or tremor, manic-depressive illness, panic attacks and psychosis are characterized by aberrant neuronal activity, which may be alleviated by controlled hypothermia.

Another aspect of the invention is the control of central nervous system swelling and inflammation. In this regard, the implantable heat transfer device behaves essentially as a controlled internal cold "compress". Cold therapy is well-know for the treatment of swelling and the invention provides for a finely regulated means for achieving cold therapy. For example, swelling of brain or spinal tissue due to trauma, hemorrhage, encephalitis or localized myelitis, mass lesions, such as tumors, cysts, and abscesses may be reduced or eliminated by cooling of the affected tissue according to the invention. Likewise, intractable migraine headaches may be controlled by hypothermia according to the invention.

The method for controlling brain or spinal tissue swelling and/or inflammation by controlled cooling would be executed essentially as described for brain cooling to regulate seizures. Briefly, the method would comprise surgically cutting a heat transfer aperture into a patient's skull or spine, thereby exposing a predetermined portion of patient's brain or spinal cord. A heat pump having one or more cell activity sensor elements and one or more temperature sensor elements would be surgically implanted into said heat transfer aperture. The heat transfer management unit would be attached such that a micro controller of the heat transfer management unit would be connected to one or more electrical sensor elements and one or more temperature sensor elements would contact brain or spinal cord tissue. The heat transfer management unit would be connected to said heat pump via a lead bundle. Responsive to signals from one or more sensor elements, mathematical algorithms of the heat transfer management unit would determine abnormal brain or spinal cord activity, causing the heat pump to transfer heat from the brain or spinal cord to a heat sink, thereby effecting cooling.

The invention is envisioned as a means to control swelling, inflammation or localized pain in non-central nervous system organs. Regionally or locally directed cooling to thoracic and abdominal organs, including the liver and intestine, as well as to skeletal muscle may control pain, swelling, or inflammation associated with these organs. To this end, a heat pump and a heat transfer management unit may be surgically implanted in, for example, a patient's abdomen, utilizing essentially the same methodology described herein for directed brain hypothermia. Briefly, the procedure would be initiated by cutting an incision into a patient's musculature, fascia and body cavity linings and skin, thereby exposing a predetermined portion of said organ. Thereafter, a heat pump having one or more activity sensor elements and one or more temperature sensor elements would be surgically implanted through this incision. A heat transfer management unit would be attached such that a micro controller of the heat transfer management unit is connected to one or more activity sensor elements and one or more temperature sensor elements in contact with organ tissue. A lead bundle would connect the heat transfer management unit to said heat pump. Responsive to signals from one or more activity or temperature sensor elements, mathematical algorithms of the heat transfer management unit detect abnormal organ cell activity Such abnormal activity causes the micro controller in the heat transfer management unit to direct the heat pump to initiate cooling to quash, for example, nociceptor activity associated with swelling, inflammation and pain.

The invention is also envisioned as a method of controllably warming a hypothermic brain. Warming may be accomplished by heat transfer to brain tissue using a surgically implanted heat transfer and detection apparatus essentially as described hereinabove for brain cooling. Abnormally low brain cell firing may be detected and monitored by electrical sensor units implanted into a hypothermic brain. The heat transfer management unit may be surgically implanted into a patient's body cavity, or may optionally be located external to a patient's body. Responsive to signals from one or more electrical sensor elements, mathematical algorithms of the heat transfer management unit would determine abnormal brain activity, causing the heat pump to transfer heat to the brain tissue from a heat source, thereby heating the patient's brain. The advantage of this method would be to permit controllable warming based upon the level of brain activity, and would avoid overheating or warming a hypothermic brain too rapidly. Such treatments could be of use either in the setting of environmental or surgical hypothermia.

Figure 2:
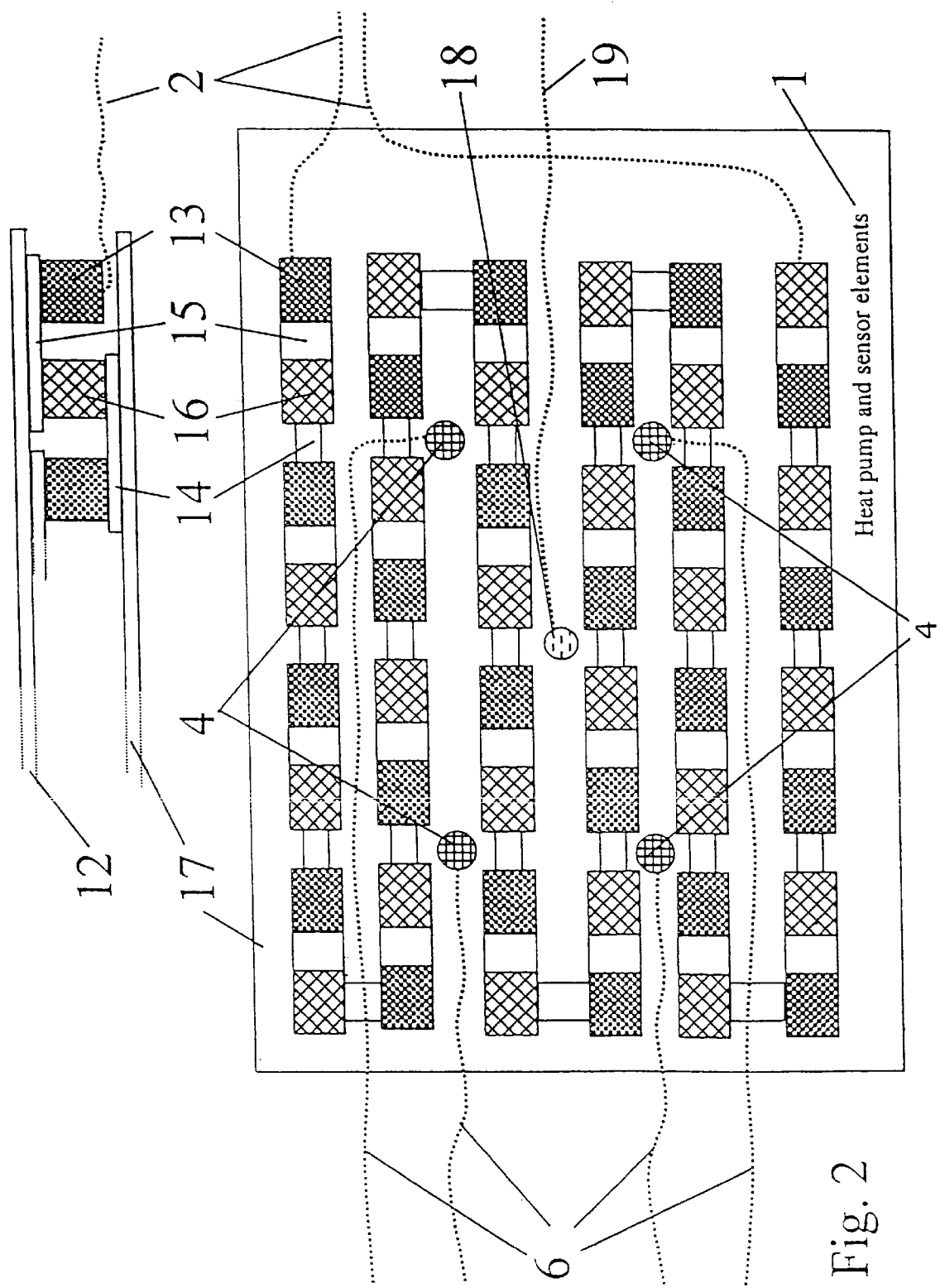
FIG. 2 shows the heat pump array of Peltier junctions combined with sensor elements which signal the HTMU to provide heat management in response to abnormal electrical brain activity.
Figure 3:
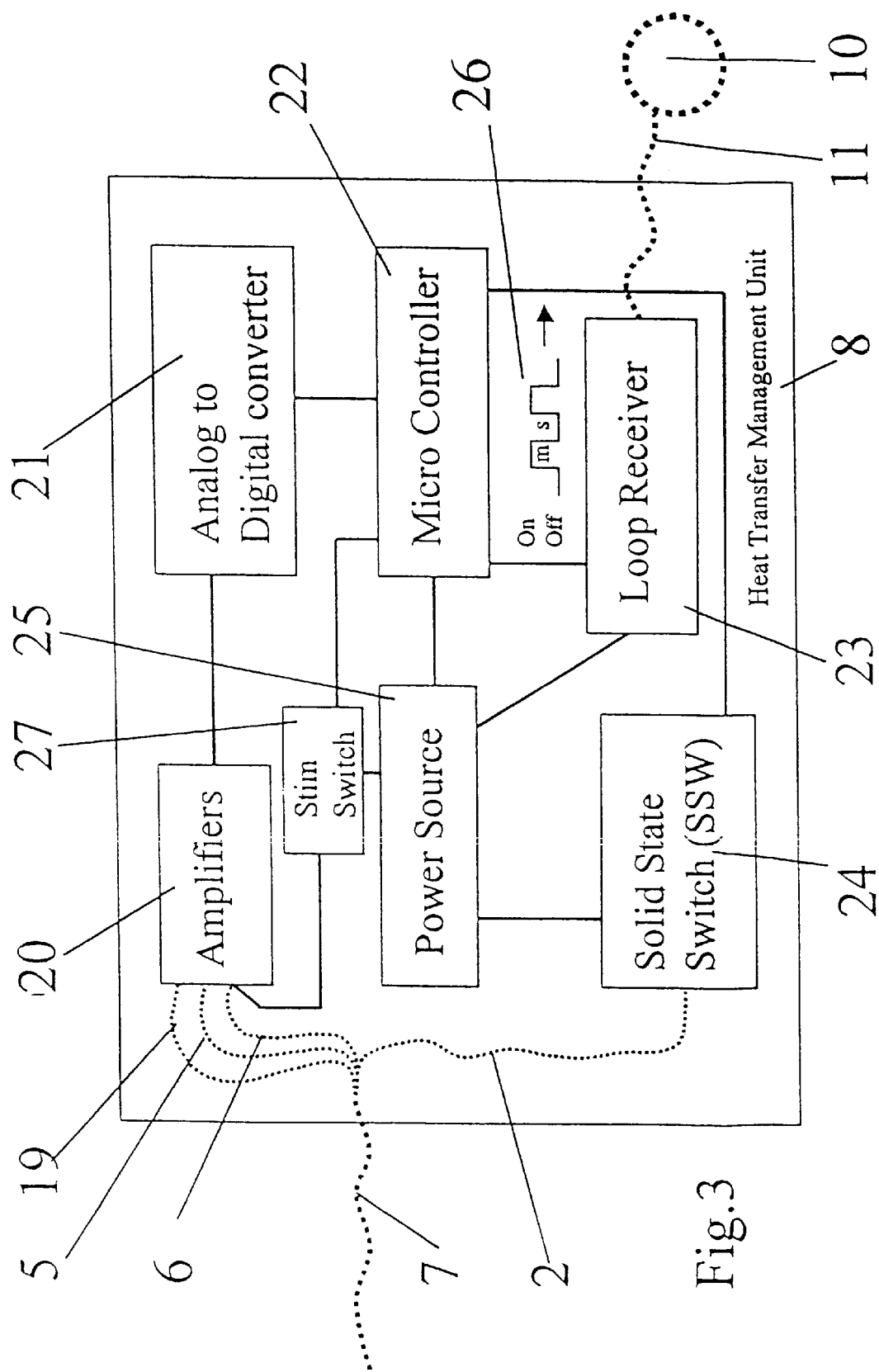
FIG. 3 shows the components of the HTMU that analyze signals from the sensor elements and activate the heat pump when required.

Referring to FIGS. 1–3, in which numerals represent like parts, in FIG. 1 heat pump 1 is shown placed in a HTA surgically cut into the patient's skull. The heat pump has sensor elements 4 and 18 for detecting abnormal brain activity and brain surface temperature, respectively. The relationship between these components is detailed in FIG. 2. In addition, activity sensor elements 3 resting on the surface of the brain monitor background brain activity. Signals generated by activity sensor element 3 are used by the micro controller 22 (shown in FIG. 3) in the HTMU 8 to determine when cooling, and possibly heating, may be necessary for controlling seizures. One or more of sensor elements 3, 4, 18 may be present, depending upon the needs of the individual patient. Sensor elements 3a, 4a, 18a may extend to regions beneath the surface of the brain, when clinically advantageous. Thus, heat transfer may also be controlled by brain temperature as detected by sensors implanted within the brain. Heat pump 1 has leads 2 that connect to a lead bundle 7, which, in turn, connects to the HTMU 8. Electrical and temperature sensor leads 5, 6, 19 feed into a lead bundle 7 that in turn connects to the HTMU 8. The HTMU 8 may be implanted in the patient's abdomen, a subcutaneous pocket, or a subclavicular pocket.

Neural cooling is achieved by using the heat pump 1 to remove heat from the brain into heat sink 9. Heat sink 9 is comprises a sac of high heat conductivity compound, such as silicon oxide paste. The heat sink sac comprises a thin, biologically inert flexible material that permits substantial heat flow. Heat sink 9 covers a larger area than the HTA, thereby allowing heat dissipation from the body through a large part of the scalp. The large area in relation to the HTA and high thermal conductivity of the sink enable more heat to dissipate from the body for a given increase in temperature output from heat pump 1 than would otherwise occur. This configuration, in turn, improves the efficiency of the heat pump 1.

Details of heat pump 1 are shown in FIG. 2. A solid state heat pump using the Peltier effect is illustrated. However, other small mechanical and/or chemical devices are suitable for heat exchange, as long as such devices could be incorporated into a patient's body and the power supply and environmental requirements of these devices may be satisfied post-implantation. Peltier junctions 13,15,16 and 16,14, 13 are sandwiched between two ceramic plates 17, 12 having high thermal conductivity. Electrical current passing through upper junctions 15 heats these junctions, while lower junctions 14 near the brain surface become cold. Thus, the Peltier effect pumps heat from the lower junctions to the upper junctions away from the brain to effect cooling. Reversal of current direction causes heat flow to the brain. Complete assemblies of Peltier junction heat pumps are well known and are readily available. The electrical current for the heat pump 1 is supplied through leads 2 that are routed through lead bundle 7 that in turn connects to the HTMU 8.

In a preferred embodiment of this invention, activity sensors 4 and a temperature sensor 18 are added to the lower ceramic plate 17 resting on the brain surface. Activity sensors 4 have leads 6 connecting the sensors to lead bundle 7, which in turn connects to the HTMU 8. Similarly, temperature sensor 18 has a lead 19, that is routed to lead bundle 7 and thereafter to the HTMU 8. Activity sensors 4 exhibit dual functions in that they may provide electrical stimulation to the brain as well as sensing electrical brain activity. Electrical stimulation occurs together with heat pumping to control seizures. Temperature sensor 18 serves two functions. First, temperature sensor 18 may trigger heat pumping to prevent a seizure should brain temperature indicate a seizure is imminent. Second, temperature sensor 18 regulates the amount of heat pumping achieved to prevent tissue damage. Although brain cooling is generally neuro-protective, too much brain cooling may result in tissue damage.

The details of the HTMU 8 are show in FIG. 3. Sensor signal leads 5,6,19 are fed to amplifiers 20, and then connect to analog to digital converter 21. Micro controller 22 then analyzes the digital representations of the sensor signals. When a seizure appears imminent, the micro controller 22 operates a solid state switch (SSW) 24 to feed power to heat pump 1, thereby preventing a seizure from occurring. Micro controller 22 uses a variable mark space waveform 26 to operate the SSW. This configuration allows variable levels of power to be applied to the heat pump while at the same time reducing the power wasted in the regulating element, SSW 24.

Power source 25 is contained in the HTMU 8 and may comprise a primary battery or a rechargeable cell. Additional power may be provided by a subcutaneous coil or induction loop 10, connected to loop receiver 23 in the HTMU 8 by lead 11. Loop receiver 23 serves to direct additional power from the induction loop, and commands and configures changes for micro controller 22. The additional power and/or commands and configuration changes come from an external unit that would transmitted by magnetic induction. Data may also be transmitted from the implanted device to the external unit in a similar fashion.

Seizures may be controlled by electrical stimulation, drug infusion or both combined with heat pumping. Electrical stimulation or infusion of therapeutic agent may be directed to any brain area associated with seizures, including the neocortex, hippocampus, amygdala thalamus, hypothalamus, caudate or other nuclei of the basal ganglia, cerebellum and brain stem. Stimulation switch 27 is provided for this purpose, according to the invention. Switch 27 is activated by micro controller 22, which sends a current pulse through lead 6 to activity sensing electrode 4. Medications could be delivered to the brain via an implanted catheter or similar tubing in the same manner. Accordingly, switch 27 is activated by micro controller 22 and in turn initiates delivery a quantity of medication through tubing onto or into the brain 28 (shown in FIG. 1). A refillable reservoir on the surface of the head permits replenishment of the medication, in a manner analogous to the functions of certain types of shunts. Switch 27 could be a single, multi-purpose switch or may be several switches, one for each purpose of initiating electrical stimulation and initiating medication delivery.

The invention is further illustrated by the following non-limiting example.

EXAMPLE

The effects of cooling neural tissue on seizure development were investigated using an EAAC1 knockout rat model of epilepsy. EACC1 antisense DNA was continuously infused into the left ventricle of a test animal for 10 days using a pump located on the animal's back. Diffuse glutamate toxicity is thereby effected in the brain of the knockout rat. Diffuse glutamate activity produced seizures, manifested by activity arrest, staring, and rhythmic 2–3/sec epileptiform EEG patterns, all indicative of seizure activity. Thereafter, the test animal was anesthetized and a cooling unit adhered to the rat's head. Due to the thinness of rat crania, cooling of the brain was achieved through the intact rat skull. EEG tracings were made at baseline (28.8° C.) and hypothermic (25.2° C.) temperatures of the conscious rat. An overall reduction in seizure activity was observed after cooling, marked by the return of normal exploratory behavior and normal EEG tracings.

While the invention has been described in detail and with reference to specific embodiments thereof, it will be apparent to those of ordinary skill in the art that various changes and modifications can be made therein without departing from the spirit and scope of the invention.

The content of all books, journal articles, abstracts and the like cited herein are hereby incorporated herein by reference.

REFERENCE

1. ANNEGERS J F (1998) Demographics and Cost of Epilepsy. *The American J of Managed Care*, 4, S453–S462.
2. BATTISTA A F (1967) Effect of Cold on Cortical Potentials in Cats. *Experimental Neurology*, 19, 140–155.
3. BEGLEY C E, ANNEGERS J F, LAIRSON D R, REYNOLDS T F, HAUSER W A (1994) Cost of epilepsy in the United States: A model based on incidence and prognosis. *Epilepsia*, 35, 1230–1243.
4. BEN-MENACHEM E, MANON-ESPAILLAT R, RISTANOVIC R, WILDER B J, STEFAN H, MIRZA W, et al (1994) Vagus nerve stimulation for treatment of partial seizures: 1. A controlled study of effect on seizures. *Epilepsia*, 35, 616–626.
5. BERNTMAN L, WELSH F A, HARP J R (1981) Cerebral Protective Effect of Low-Grade Hypothermia. *Anesthesiology*, 55, 495–498.
6. BIGELOW W G, LINDSAY W K, GREENWOOD W F (1950) Hypothermia. Its Possible Role in Cardiac Surgery: An Investigation of Factors Governing Survival in Dogs at Low Body Temperatures. *Ann Surg*, 132, 849–866.
7. BUSTO R, GLOBUS M Y T, DIETRICH W D, MARTINEZ E, VALDES I, GINSBURG M D (1989) Effect of Mild Hypothermia on Ischemia-Induced Release of Neurotransmitters and Free Fatty Acids in Rat Brain. *Stroke*, 20, 904–910.
8. CLIFTON G L, JIANG J Y, LYETH B G, JENKINS L W, HAMM R J, HAYES R L (1991) Marked Protection by Moderate Hypothermia After Experimental Traumatic Brain Injury. *J Cerebral Blood Flow & Metabolism*, 11, 114–121.
9. DEPAULIS E A (1994) Endogenous Control of Epilepsy: The Nigral Inhibitory System. *Progress in Neurobiology*, 42, 33–52.
10. EDMONDS H L, STARK L G, HOLLINGER M A (1974) The Effects of Diphenylhydantoin, Phenobarbital, and Diazepam on the Penicillin-Induced Epileptogenic Focus in the Rat. *Experimental Neurology*, 45, 377–386.
11. ENGEL J, JR. (1993) *Surgical Treatment of the Epilepsies*. New York: Raven Press.
12. ESSMAN W B, SUDAK F N (1964) Audiogenic Seizure in Genetically Susceptible Mice: Relation of Hypothermia to Onset and Susceptibility. *Experimental Neurology*, 9, 228–235.
13. FISHER R S, UEMATSU S, KRAUSS G L, CYSYK B J, LESSER R P, RISE M (1992) A Controlled Pilot Study of Centromedian Thalamic Stimulation for Epilepsy. *Epilepsia*, 33, 841–851.
14. FISHER R S, KRAUSS G L, RAMSAY E, LAXER K, GATES J (1997) Assessment of vagus nerve stimulation for epilepsy: Report of the therapeutics and technology assessment subcommittee of the American Academy of Neurology. *Neurology*, 49, 293–297.
15. GALE (1985) Mechanisms of Seizure Control Mediated by Gamma-Aminobutyric Acid: Role of the Substantial Nigra. *Federal Proceedings*, 44, 2414–2424.
16. GARTSIDE I B (1978) The Actions of Diazepam and Phenytoin on a Low Dose Penicillin Epileptiform Focus in the Anaesthetised Rat. *British J Pharmacology*, 62, 289–292.
17. GOTMAN J, LEVTOVA V (1996) Amygdala-Hippocampus Relationships in Temporal Lobe Seizures: A Phase-Coherence Study. *Epilepsy Research*, 25, 51–57.
18. GUNN A J, GLUCKMAN P D, GUNN T R (1998a) Selective Head Cooling in Newborn Infants After Perinatal Asphyxia: A Safety Study. *Pediatrics*, 102, 885–892.
19. GUNN A J, GUNN T R, GUNNING M I, WILLIAMS C E, GLUCKMAN P D (1998b) Neuroprotection with Prolonged Head Cooling Started Before Postischemic Seizures in Fetal Sheep. *Pediatrics*, 102, 1098–1106.
20. HAUSER W A, ANNEGERS J F, KURLAND L T (1993) Incidence of epilepsy and unprovoked seizures in Rochester, Minn.: 1935–1984. *Epilepsia*, 34, 453–468.
21. HAUSER W A, HESDORFFER D C (1990) *Epilepsy: Frequency, Causes and Consequences*, New York: Demos Publications.
22. HIRAI T, JONES E G (1989) A New Parcellation of the Human Thalamus on the Basis of Histochemical Staining. *Brain Research Review*, 14, 1–34.
23. IASEMIDIS L D, SACKELLARES J C, ZAVERL H P, WILLIAMS W J (1990) Phase Space Topography and the Lyapunov Exponent of Electrocorticograms in Partial Seizures. *Brain Topography*, 3, 1–15.
24. ITO T, HORI M, YOSHIDAl K, SHIMIZU M (1977) Effect of Anticonvulsants on Cortical Focal Seizure in Cats. *Epilepsia*, 18, 63–71.
25. LEES G P, LORING D W, SMITH J R, FLANIGIN H F (1995) Intraoperative Hippocampal Cooling and Wada Memory Testing in the Evaluation of Amnesia Risk Following Anterior Temporal Lobectomy. *Arch Neurology*, 52, 857–861.
26. LEHNERTZ K, ELGER C E (1998) Can Epileptic Seizures Be Predicted: Evidence from Nonlinear Time Series Analysis of Brain Electrical Activity. *Physiol Rev Lett,* 80, 5019–5022.
27. LESSER R P, KIM S H, BEYDERMAN L, KRAUSS G, CYSYK B, SANDERS P (1998) Pulse Stimulation Can Stop Bursts of Afterdischarges in Humans. *Epilepsia,* 39, 200(Abstract)
28. MARES P, KOLINOVA M, FISCHER J (1998) The Influence of Pentobarbital Upon a Cortical Epileptogenic Focus in Rats. *Arch int Pharmacodyn,*
29. MARION D W, PENROD L E, KELSEY S F, OBRIST W D, KOCHANEK P M, PALMER A M, et al (1997) Treatment of Traumatic Brain Injury with Moderate Hypothermia. *New England Journal of Medicine,* 336, 540546
30. MARTINERIE J, ADAM C, LE VAN QUYEN M, BAULAC M, CLEMENCEAU S, RENAULT B, et al (1998) Epileptic Seizures Can Be Anticipated by Non-Linear Analysis. *Nature Medicine,* 4, 1173–1176.
31. MINAMISAWA H, SMITH M L, SIESJÖ B K (1990) The effect of mild hyperthermia and hypothermia on brain damage following 5, 10, and 15 minutes of forebrain ischemia. *Annals of Neurology,* 28, 26–33.
32. MIRSKI M A, ROSSELL L A, TERRY J B, FISHER R S (1997) Anticonvulsant Effect of Anterior Thalamic High Frequency Electrical Stimulation in the Rat. *Epilepsy Research,* 28, 89–100.
33. MIRSKI M A, FERRENDELLI J A (1986) Selective Metabolic Activation of the Mammillary Bodies and Their Connections During Ethosuximide-Induced Suppression of Pentylenetetrazol Seizures. *Epilepsia,* 27, 194–203.
34. MIRSKI M A, FISHER R S (1994) Electrical Stimulation of the Mammillary Nuclei Increases Seizure Threshold to Pentylenetetrazol in Rats. *Epilepsia,* 35, 1309–1316.
35. OMMAYA A K, BALDWIN M (1963) Extravascular Local Cooling of the Brain in Man. *J Neurosurgery,* 20, 8–20.
36. OSORIO I, FREI M G, WILKINSON S B (1998) Real-time automated detection and quantitative analysis of seizures and short-term prediction of clinical onset. *Epilepsia,* 39, 615–627.
37. QU H, GOTMAN J (1993) Improvement in Seizure Detection Performance by Automatic Adaptation to the EEG of Each Patient. *Electroencephalo and clin Neurophysiol,* 86, 79–87.
38. SCHIFF E A (1994) Controlling Chaos in the Brain. *Nature,* 340, 615–620.
39. SUSSMAN N M, GOLDMAN H W, JACKEL R A, KAPLAN L, CALLANAN M, BERGEN J, et al (1988) Anterior thalamic stimulation in medically intractable epilepsy. Part II. Preliminary Clinical Results. *Epilepsia,* 29, 677(Abstract)
40. VASTOLA E F, HOMAN R, ROSEN A (1969) Inhibition of Focal Seizures by Moderate Hypothermia. *Archives of Neurology,* 20,430–439.
41. VELASCO F, VELASCO M, OGARRIO C, FANGHANEL G (1987) Electrical stimulation of the centromedian thalamic nucleus in the treatment of convulsive seizures: a preliminary report. *Epilepsia,* 28, 421–430.
42. WEBBER W R, LITT B, WILSON K, LESSER R P (1994) Practical detection of epileptiform discharges (EDs) in the EEG using an artificial neural network: a comparison of raw and parameterized EEG data. *Electroencephalography and Clinical Neurophysiology,* 91, 194–204.
43. WEBBER W R S, LESSER R P, RICHARDSON R T, WILSON K (1996) An Approach to Seizure Detection using an Artificial Neural Network (ANN). *Electroenceph clin Neurophysiol,* 98, 250–272.

What is claimed is:

1. A method of treating a brain disorder by heat transfer from brain tissue comprising the steps of:
   surgically cutting a heat transfer aperture into a patient's skull, thereby exposing a predetermined portion of patient's brain;
   surgically implanting into said heat transfer aperture a heat pump having one or more activity sensor elements and one or more temperature sensor elements;
   surgically implanting a heat transfer management unit in a body cavity of said patient such that a micro controller of the heat transfer management unit is connected to one or more activity sensor elements and one or more temperature sensor elements contact brain tissue; and
   connecting the heat transfer management unit to said heat pump via a lead bundle;
      whereby responsive to signals from one or more activity sensor elements, mathematical algorithms of the heat transfer management unit determine abnormal brain activity, causing the heat pump to remove heat from the brain tissue into a heat sink, thereby cooling the predetermined portion of the patient's brain.

2. A method according to claim 1, wherein heat transfer is controlled by brain temperature as detected by one or more temperature sensor elements, thereby preventing excessive heat transfer either into or out of the brain.

3. A method according to claim 2, wherein brain temperature is detected by sensors located at the brain surface or implanted within the brain.

4. A method according to claim 2, wherein control of heat transfer may be initiated by external agents via an induction loop which sends signals to the heat transfer management unit.

5. A method according to claim 1, wherein said heat pump uses Peltier junctions to achieve heat transfer.

6. A method according to claim 1, wherein said heat transfer management unit is implanted in a body cavity selected from the group consisting of abdomen, a subcutaneous pocket and a subclavicular pocket.

7. A method according to claim 1, wherein said heat sink comprises silicon oxide paste contained in a thin sac of biologically inert material.

8. A method according to claim 1, whereby power to operate the heat pump may be provided by at least one member selected from the group consisting of internal batteries, internal rechargeable cells, a subcutaneous coil, a subcutaneous induction loop, an external power source having an induction loop and a combination of internal and an external power sources.

9. A method according to claim 1, wherein said brain disorder comprises a member selected from the group consisting of epilepsy, intractable pain, psychiatric disorders and movement disorders.

10. A method according to claim 1, wherein activity sensors on ceramic plates implanted in or on the brain detect or predict seizure occurrence by analyzing brain activity via analysis with an algorithm, wherein such detection promotes heat pump-mediated brain cooling to reduce or prevent seizure initiation and/or propagation.

11. A method of reducing or preventing the occurrence of a seizure comprising cooling brain tissue according to claim 1, and electrically stimulating the brain at or near a seizure focus or a structure that modulates seizures.

12. A method of reducing or preventing the occurrence of a seizure comprising cooling brain tissue according to claim 1, and infusing a therapeutic agent into the brain at or near a seizure focus or a structure that modulates seizures.

13. A method of reducing or preventing the occurrence of a seizure comprising cooling brain tissue according to claim 1, electrically stimulating the brain at or near a seizure focus or a structure that modulates seizures, and infusing a therapeutic agent into the brain at or near a seizure focus or a structure that modulates seizures.

14. A method according to any one of claims 11–13, wherein said electrical stimulation or said infusion of therapeutic agent is directed to a brain area comprising a member selected from the group consisting of neocortex, hippocampus, amygdala thalamus, hypothalamus, caudate or other nuclei of the basal ganglia, cerebellum and brain stem.

15. A method according to claim 12 or claim 13, wherein said therapeutic agent comprises a member selected from the group consisting of hydantoins, deoxybarbiturates, benzodiazepines, glutamate receptor agonists, glutamate receptor antagonists, γ-aminobutyric acid receptor agonists, γ-aminobutyric acid receptor antagonists, dopamine receptor agonists, dopamine receptor antagonists and anesthetics.

16. A method of controllably warming a hypothermic brain by heat transfer to brain tissue comprising the steps of:

surgically cutting a heat transfer aperture into a patient's skull, thereby exposing a predetermined portion of patient's brain;

surgically implanting into said heat transfer aperture a heat pump having one or more activity sensor elements and one or more temperature sensor elements;

attaching a heat transfer management unit such that a micro controller of the heat transfer management unit is connected to one or more activity sensor elements and one or more temperature sensor elements contact brain tissue; and connecting the heat transfer management unit to said heat pump via a lead bundle;

whereby responsive to signals from one or more activity sensor elements, mathematical algorithms of the heat transfer management unit determine abnormal brain activity, causing the heat pump to transfer heat to the brain tissue from a heat source, thereby heating the patient's brain.

17. A method according to claim 16, wherein said heat transfer management unit is surgically implanted into a patient's body cavity or is located external to a patient's body.

18. A method for control of central nervous system tissue swelling or inflammation by controlled cooling comprising the steps of:

surgically cutting a heat transfer aperture into a patient's skull or spine, thereby exposing a predetermined portion of patient's brain or spinal cord;

surgically implanting into said heat transfer aperture a heat pump having one or more activity sensor elements and one or more temperature sensor elements;

attaching a heat transfer management unit such that a micro controller of the heat transfer management unit is connected to one or more members of the group consisting of activity sensor elements and temperature sensor elements contacting brain or spinal cord tissue; and connecting the heat transfer management unit to said heat pump via a lead bundle;

whereby responsive to signals from said one or more activity sensor elements or one or more temperature sensor elements, mathematical algorithms of the heat transfer management unit determine abnormal brain or spinal cord activity, causing the heat pump to transfer heat from the brain or spinal cord tissue to a heat sink, thereby effecting cooling.

19. A method according to claim 18, wherein said central nervous system tissue swelling or inflammation is due to a member selected from the group consisting of trauma, hemorrhage, encephalitis, localized myelitis, mass lesions and intractable migraine headaches.

20. A method of controlling swelling, inflammation or localized pain in a non-central nervous system organ by regionally or locally directed cooling to said organ comprising the steps of:

surgically cutting an incision into a patient's musculature, fascia and body cavity linings and skin, thereby exposing a predetermined portion of said organ;

surgically implanting through this incision a heat pump having one or more activity sensor elements and one or more temperature sensor elements;

attaching a heat transfer management unit such that a micro controller of the heat transfer management unit is connected to one or more activity sensor elements and one or more temperature sensor elements in contact with organ tissue; and connecting the heat transfer management unit to said heat pump via a lead bundle;

whereby responsive to signals from said one or more activity or temperature sensor elements, mathematical algorithms of the heat transfer management unit detect abnormal organ cell activity, causing the heat pump to transfer heat from the organ tissue to a heat sink, thereby cooling the patient's organ to reduce or eliminate swelling, inflammation or localized organ pain.

21. A method according to claim 20, wherein said non-central nervous system organ comprises a member selected from the group consisting of thoracic and abdominal organs and skeletal muscle.

* * * * *